United States Patent [19]

Machold et al.

[11] Patent Number: 5,458,574

[45] Date of Patent: Oct. 17, 1995

[54] SYSTEM FOR PERFORMING A CARDIAC PROCEDURE

[75] Inventors: Timothy R. Machold, Moss Beach; Wesley D. Sterman, San Francisco, both of Calif.

[73] Assignee: Heartport, Inc., Redwood City, Calif.

[21] Appl. No.: 213,760

[22] Filed: Mar. 16, 1994

[51] Int. Cl.⁶ .................................................. A61M 29/00
[52] U.S. Cl. .............................. 604/101; 604/53; 606/194
[58] Field of Search ............................. 604/96, 101, 104, 604/53, 49, 264, 280; 606/191–194; 128/656, 657, 658

[56] References Cited

U.S. PATENT DOCUMENTS

| | | | |
|---|---|---|---|
| 4,276,874 | 7/1981 | Wolvek et al. | 128/1 D |
| 4,527,549 | 7/1985 | Gabbay | 128/1 D |
| 4,531,936 | 7/1985 | Gordon | 604/49 |
| 4,592,340 | 6/1986 | Boyles | 128/1 D |
| 4,664,125 | 5/1987 | Pinto | 128/672 |
| 4,697,574 | 10/1987 | Karcher et al. | 128/1 D |
| 4,705,507 | 11/1987 | Boyles | 604/101 |
| 4,741,328 | 5/1988 | Gabbay | 128/1 D |
| 4,785,795 | 11/1988 | Singh | 600/18 |
| 4,861,330 | 8/1989 | Voss | 600/18 |
| 4,877,035 | 10/1989 | Bogen et al. | 128/673 |
| 4,902,272 | 2/1990 | Milder et al. | 600/18 |
| 4,902,273 | 2/1990 | Choy et al. | 600/18 |
| 4,943,275 | 7/1990 | Stricker | 600/18 |
| 5,011,469 | 4/1991 | Buckberg et al. | 604/4 |
| 5,122,115 | 6/1992 | Marks | 604/53 |
| 5,166,305 | 5/1992 | Milder et al. | 600/18 |
| 5,167,628 | 12/1992 | Boyles | 604/101 |
| 5,176,619 | 1/1993 | Segalowitz | 600/18 |
| 5,195,942 | 3/1993 | Weil et al. | 600/18 |
| 5,226,889 | 7/1993 | Sheiban | 604/101 |
| 5,304,135 | 4/1994 | Shonk | 606/194 X |
| 5,308,319 | 5/1994 | Ide et al. | 604/53 X |
| 5,308,320 | 5/1994 | Safar et al. | 604/4 |
| 5,308,323 | 5/1994 | Sogawa et al. | 604/96 X |
| 5,312,344 | 5/1994 | Grinfeld et al. | 604/101 |

FOREIGN PATENT DOCUMENTS

| | | |
|---|---|---|
| 0218275 | 4/1987 | European Pat. Off. . |
| 9217118 | 10/1992 | WIPO . |

OTHER PUBLICATIONS

Peters, W. S., "Minimally Invasive Cardiac Surgery By Cardioscopy" *Austral. As. J. Cardiac Thorac. Surg.*, 1993, 2:3:152–154.

Mediteach©, Instructions for Use, Occlusion Balloon Catheters Rev. Mar. 1991. pp. 1–7.

Uchida, Y. et al. "Percutaneous cardiomyotomy and valvulotomy with angioscopic guidance," Amer. Heart J., Apr. 1991, pp. 1222–1224.

Uchida, Y. et al. "Percutaneous fiberoptic angioscopy of the cardiac valves," American Heart Journal, Jun. 1991, pp. 1791–1798.

(List continued on next page.)

Primary Examiner—John D. Yasko
Attorney, Agent, or Firm—Townsend and Townsend and Crew

[57] ABSTRACT

A system for accessing a patient's cardiac anatomy which includes an occlusion catheter with a first expandable member or balloon in a distal extremity of the catheter which when expanded within the patient's ascending aorta separates the heart and coronary blood vessels from the rest of the patient's arterial system, and a second expandable member, distal to the first, which when expanded will be seated within the left ventricle. A cardiopulmonary bypass system is connected to a major vein, e.g. femoral, to withdraw blood, remove carbon dioxide, oxygenate the withdrawn blood and then return the oxygenated blood to the patient's arterial system through a major artery. Preferably, the heart muscle or myocardium is paralyzed by the antegrade and/or retrograde delivery of a liquid containing cardioplegic material to the myocardium through patient's coronary arteries or coronary sinus. The cardiac accessing system is suitable for a wide variety of cardiac procedures including opened and closed chest procedures.

30 Claims, 4 Drawing Sheets

OTHER PUBLICATIONS

Yamaguchi, A., "A Case of A Reoperation Using a Balloon Catheter with Blocked Pars Ascendes Aortae," *Kyobu Geka,* Oct. 1991, 42:11:961–964.

Takahashi, M., "Retrograde Coronary Sinus Perfusion for Myocardial Protection in Aortic Valve Surgery," *J. Jpn. Assn. Thorac. Surg.,* 1982, 30:3, 306–318.

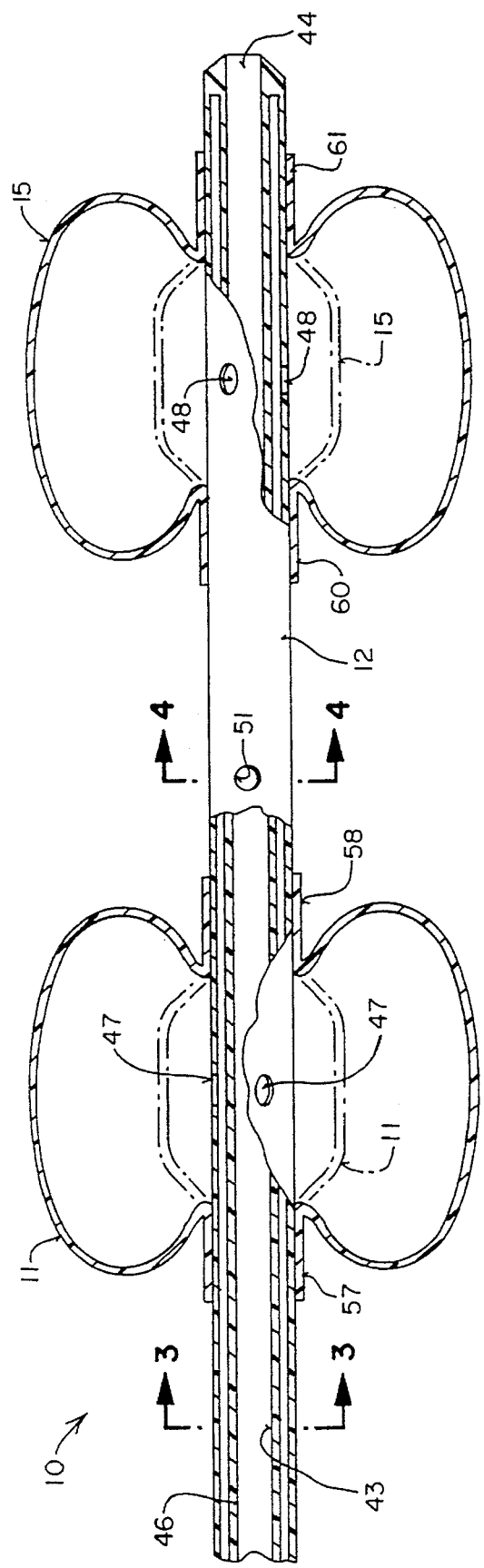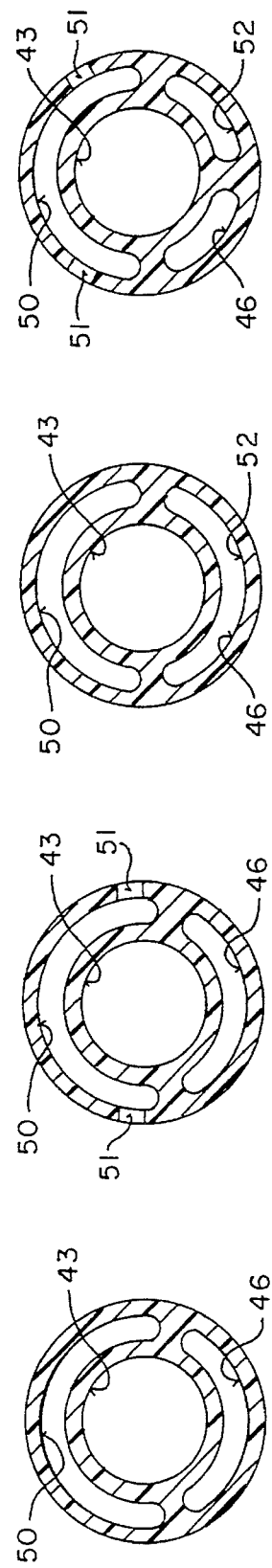

5,458,574

1

SYSTEM FOR PERFORMING A CARDIAC PROCEDURE

FIELD OF THE INVENTION

This invention relates to a catheter system which facilitates performing cardiac procedures and particularly an aortic catheter clamp which isolates the patient's heart from the patient's arterial system.

BACKGROUND OF THE INVENTION

When it is necessary to perform surgery on a patient's heart, the surgery has heretofore usually been accomplished by a major open heart surgical procedure, requiring general anesthesia and full cardiopulmonary bypass, with complete cessation of cardiopulmonary activity. Such surgery usually includes about three weeks of hospitalization and months of recuperation time for the patient. The average mortality rate with this type of procedure is about five to six percent, and the complication rate is substantially higher. Descriptions of open heart procedures can be found in *Gibbon's Surgery of the Chest*, 5th Ed., David C. Sabiston, Jr., M.D., Frank D. Spencer, M.D., 1990, Vol. II, Ch. 52, pp. 1566–1596, and *Textbook of Interventional Cardiology*, Eric J. Topol, 1990, Chs. 43–44, pp. 831–867.

In those cardiac procedures requiring cardiopulmonary bypass, a large clamp is applied to the exterior of the ascending aorta to close it off once cardiopulmonary bypass is established. However, application of such an external clamp to a calcified aorta may release emboli into the bloodstream. Further, upon the removal of the aortic clamp at the end of the procedure, any debris or thrombus generated during the procedure upstream of the clamp or by the clamp itself can travel into the brachiocephalic, the carotid, or the subclavian arteries, with serious results such as strokes and the like. For example, in up to 6% of the open-chest coronary bypass surgeries performed in the United States, there is noticeable degradation of the patient's mental faculties following such surgeries. This degradation is commonly attributed to cerebral arterial blockage from debris and emboli generated during the surgical procedure.

An endovascular system and procedure for performing cardiac surgery has been described in copending applications Ser. Nos. 07/730,559, filed on Jul. 16, 1991, 07/991,188, filed on Dec. 15, 1992, and 08/123,411, filed Sep. 17, 1993, the disclosures of which are hereby incorporated herein by reference. In these patent applications, an endovascular clamp is described which isolates the patient's heart from the patient's arterial system without the need for a thoracotomy. The endovascular clamp is an elongated intra-aortic catheter which is introduced into the patient's femoral artery and which has an occlusive balloon on a distal portion of the catheter. In the procedure described, the catheter is advanced through the patient's femoral artery and aorta until the occlusive balloon on the distal portion of the catheter is disposed within the patient's ascending aorta at a location between the coronary artery ostia and the brachiocephalic artery. The occlusive balloon is inflated or otherwise expanded in this region to occlude the aortic passageway and is maintained in the expanded condition until the completion of the procedure. The patient is placed on cardiopulmonary bypass to maintain circulation of oxygenated blood. Cardioplegic material is then introduced into the myocardium of the patient's heart either antegradely through one or both of the coronary arteries or retrogradely through the patient's coronary sinus or both. Following completion of the procedure, the region upstream from the occlusion balloon including the ascending aorta and the patient's left ventricle may be bathed in irrigation fluid, e.g. saline solution, and the fluid and any debris or emboli in the region can be aspirated through an inner lumen of the catheter to the proximal end thereof which extends out of the patient. When the aortic region and the left ventricle are free of debris, the balloon is deflated or otherwise contracted and the catheter removed so that normal blood flow can resume.

In the short period during and after the occlusion balloon is inflated, but before the cardioplegic material paralyzes the patient's heart, significant pressure pulses from the beating heart and the cardiopulmonary bypass system are applied to both ends of the inflated occlusion balloon. This may displace the occlusion balloon from its desired position within the ascending aorta, causing damage to the aortic valve, or occluding the ostia of the coronary arteries, brachiolcephalic anew or other artery.

What has been needed and heretofore unavailable is a means to securely position the occlusion balloon within the ascending aorta so that the pressure pulses received on the ends of the occlusion balloon do not displace the balloon from its desired position. The present invention solves this and other problems.

The descriptive terms "downstream" and "upstream", when used herein in relation to the patient's vasculature, relate to the direction of normal blood flow and to the direction opposite normal blood flow through a vessel respectively, i.e., "upstream" is closer to the heart in the arterial system and further from the heart in the venous system. The terms "proximal" and "distal", when used herein in relation to instruments used in a cardiac procedure, refer to directions closer and farther away respectively from that end of the instrument which is held or manipulated by the operator performing the procedure.

SUMMARY OF THE INVENTION

The present invention is directed to an endovascular method and system for preparing a patient's heart for cardiac procedures and particularly for isolating the patient's heart from the patient's arterial system.

Essential to the invention is an endovascular catheter which has a catheter shaft with a proximal portion and a distal portion, an expandable occluding member on the distal portion of the catheter shaft, a distal port in the distal end of the catheter shaft and a first inner lumen extending within the catheter shaft from the distal port to the proximal portion of the catheter shaft. The catheter shaft is dimensioned so that a part of the distal portion of the catheter shaft may be disposed within the patient's ascending aorta and the proximal portion of the catheter shaft extends out of the patient when the catheter is properly positioned within the patient. An expandable seating member is disposed on the distal portion of the catheter shaft at a location which is spaced a sufficient distance distal to the expandable occluding member so that when the occluding member is properly positioned between the coronary ostia and the brachiocephalic artery, the seating member may be expanded and seated within the left ventricle upstream from the patient's aortic valve.

Preferably, the occluding and seating members are inflatable members and are expanded by the introduction of inflation fluid within their interiors. Although the catheter shaft may be provided with only one inflation lumen to inflate both the occlusion and seating members, it is preferred to provide separate inflation lumens for each of these expandable members so that their inflation and deflation may be independently controlled.

The catheter shaft preferably also has another inner lumen which extends from a location in the proximal catheter shaft section outside of the patient to a port in the catheter shaft located between the occluding and seating members. In this manner when the expandable occluding and seating members are expanded to block the ascending aorta and fix the catheter position therein, a diagnostic or therapeutic fluid may be introduced into the isolated region of the ascending aorta between the coronary ostia and the aortic valve through the port between the two balloons. This fluid delivery is particularly useful in delivering cardioplegic fluid into the coronary arteries through the coronary ostia. The lumen may also be used to deliver irrigation fluid into the blocked region between the expanded occlusion and seating members to facilitate removal of debris and emboli which may be formed during the procedure before the occlusion balloon is deflated at the end of the procedure. In addition, the lumen may be used for introduction of interventional devices into the aorta and/or coronary arteries to perform various diagnostic or interventional procedures.

The catheter is dimensioned and configured to be introduced into the patient's arterial system through the femoral, brachial or carotid arteries, and advanced in a retrograde manner until the occluding member on the catheter shaft is disposed within the patient's ascending aorta and the seating member on the catheter shaft is disposed within the patient's left ventricle immediately adjacent the upstream side of the aortic valve. In some embodiments, the catheter profile may be too large to be introduced percutaneously as in a Seldinger technique so a cut-down may be required. The occlusion catheter should be positioned within the ascending aorta, downstream from the coronary ostia and upstream from the brachiocephalic artery so that when the occluding member is expanded it does not block either of these arterial lumens.

When the catheter is properly positioned within the patient's ascending aorta, the distal end of the catheter extends through the patient's aortic valve so that the seating member is disposed in the left ventricle. After the seating member is expanded, the catheter shaft may be pulled downstream to seat the seating member within the left ventricle upstream of the aortic valve. The occluding member may then be expanded to occlude the ascending aorta. In this manner the catheter then becomes securely positioned within the aorta so that there is little or no movement of the occlusion balloon during the procedure, particularly when the heart is beating.

In most instances, the catheter of the pro-sent invention requires the use of a cardiopulmonary bypass system to deliver oxygenated blood to the arterial system which has been isolated from the patient's heart. Particularly attractive features of the invention include preparation of the patient's heart for a surgical procedure without the use of an external clamp on the ascending aorta, and allowing for endovascular or thoracoscopic surgery and various other procedures on the heart without the need for a thoracotomy. It should also be noted that, if, during a closed-chest endovascular cardiac procedure in accordance with the invention, it becomes necessary to perform a conventional open-chest procedure, the patient's heart is already fully prepared for the procedure. All that is necessary is to perform a thoracotomy to expose the patient's heart.

In one presently preferred embodiment of the invention directed to endovascular coronary procedures, the occlusion catheter of the invention may be used to deliver instruments for the procedures through the inner lumen and out the distal port. In these procedures, the expanded occluding member on the distal portion of the catheter sufficiently secures the distal end of the catheter within the aorta to allow for the accurate guidance of instruments to be used during the procedure.

By partitioning the arterial system with the catheter in this manner, it has been found that cardioplegic fluid can be continuously introduced into the patient's coronary arteries at very low temperatures so that the heart can be maintained in a paralyzed state for long periods without serious damage to the heart muscles. Irrigation fluid can be introduced through the distal port in the distal end of the catheter shaft to facilitate imaging, e.g. angioscopic observation, of the cardiac procedure. A continual flow of clear fluid may be directed to the surgical field in order to maintain fluid clarity sufficient for imaging the site during the procedure. The pressure of the body of irrigation fluid at the surgical site should be maintained at a level higher than the fluid pressure in the patient's left atrium to ensure that the mitral valve remains closed during the procedure and thereby prevent the intrusion of blood from the left atrium into the left ventricle which can interfere with the imaging.

The left ventricle is preferably decompressed by holding the pulmonary and tricuspid valves open by suitable means such as the catheter described in U.S. Pat. No. 4,889,137 (Kolobow) which is incorporated herein by reference. The catheter described therein is advanced through the patient's venous system, e.g. through the right internal jugular vein, the right atrium and the right ventricle into the pulmonary trunk. As described in this patent, a spring is provided on the exterior of the catheter at the locations where the catheter will extend through the pulmonary and tricuspid valves in order to hold open the valves and decompresses the left ventricle through the pulmonary capillaries. In the alternative, a pulmonary vent catheter maybe advanced in essentially the same manner as that described by Kolobow above until the distal end of the catheter is within the pulmonary trunk. The catheter may include an inflatable member near it distal which is dimensioned so that upon inflation it will block the pulmonary trunk. The trunk may then be vented through an inner lumen of the catheter which extends through the catheter from a port in its distal end to a port in its proximal end, which is located outside of the patient.

The catheter of the invention with an expandable occluding member on the distal portion and an expandable seating member distal to the occluding member provides an effective aortic clamp and, coupled with cardiopulmonary bypass, infusion of carioplegic fluid and decompression of the left ventricle, provides for a unique intravascular approach to a wide variety of cardiac procedures which do not require grossly invasive thoracic or abdominal surgery. Moreover, as mentioned, the system may even be employed in conventional open-heart procedures should it be needed. These and other advantages of the invention will become more apparent from the following detailed description of the invention when taken in conjunction with the accompanying exemplary drawings.

BRIEF DESCRIPTION OF THE DRAWINGS

FIG. 2 is a partial longitudinal cross-sectional view of the occlusion catheter shown in FIG. 1.

FIG. 3 is a transverse cross-sectional view of the catheter shaft of the occlusion catheter shown in FIG. 2 taken along the lines 3—3.

FIG. 4 is a transverse cross-sectional view of the catheter shaft of the occlusion catheter shown in FIG. 2 taken along the lines 4—4.

FIGS. 5 and 6 are transverse cross-sectional views of an alternative catheter shaft for the occlusion catheter and taken at essentially the same locations as in FIGS. 3 and 4, respectively.

DETAILED DESCRIPTION OF THE INVENTION

Figure 1:
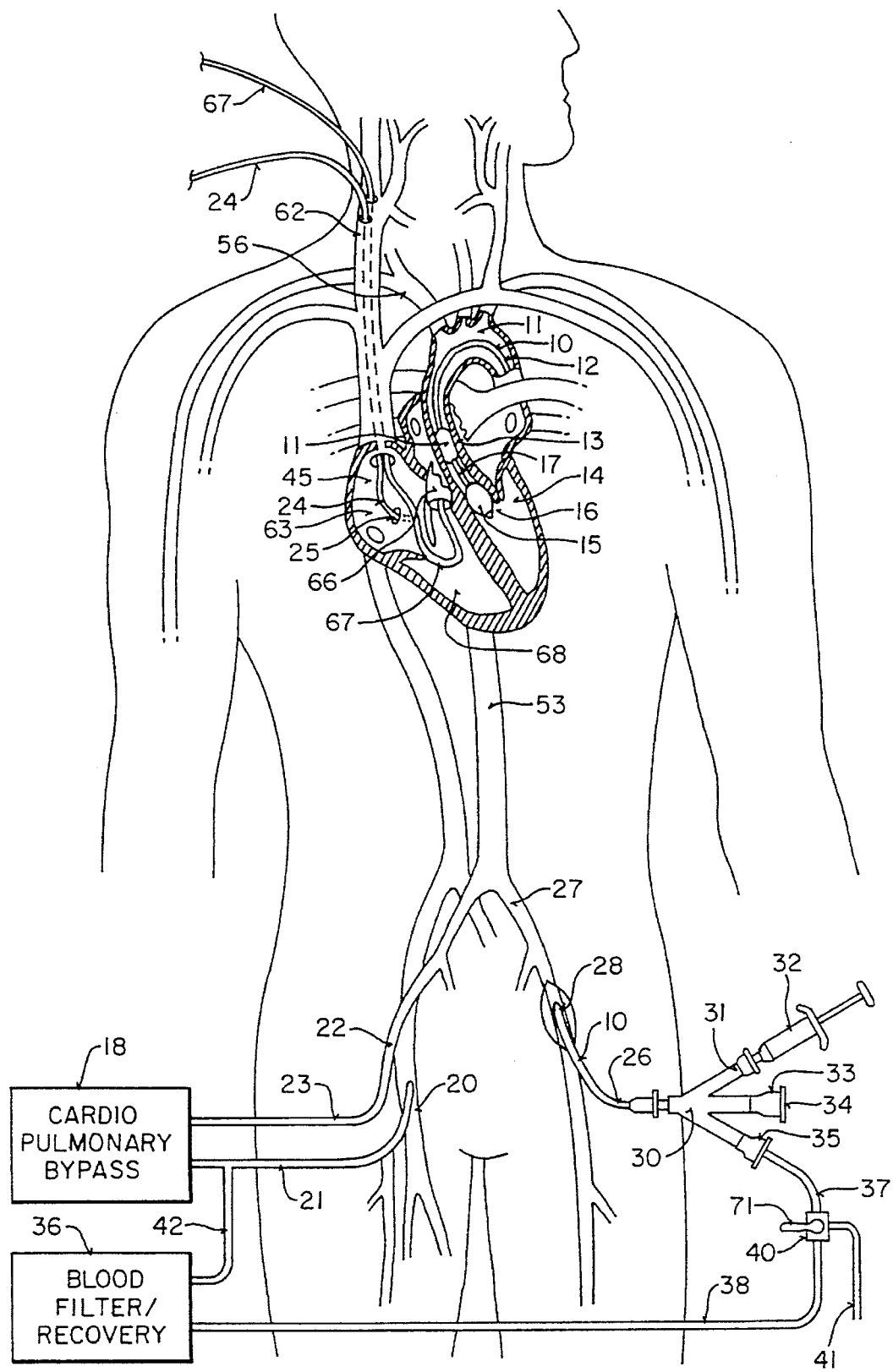
FIG. 1 schematically illustrates a cardiac access system embodying features of the invention.
Figure 7:
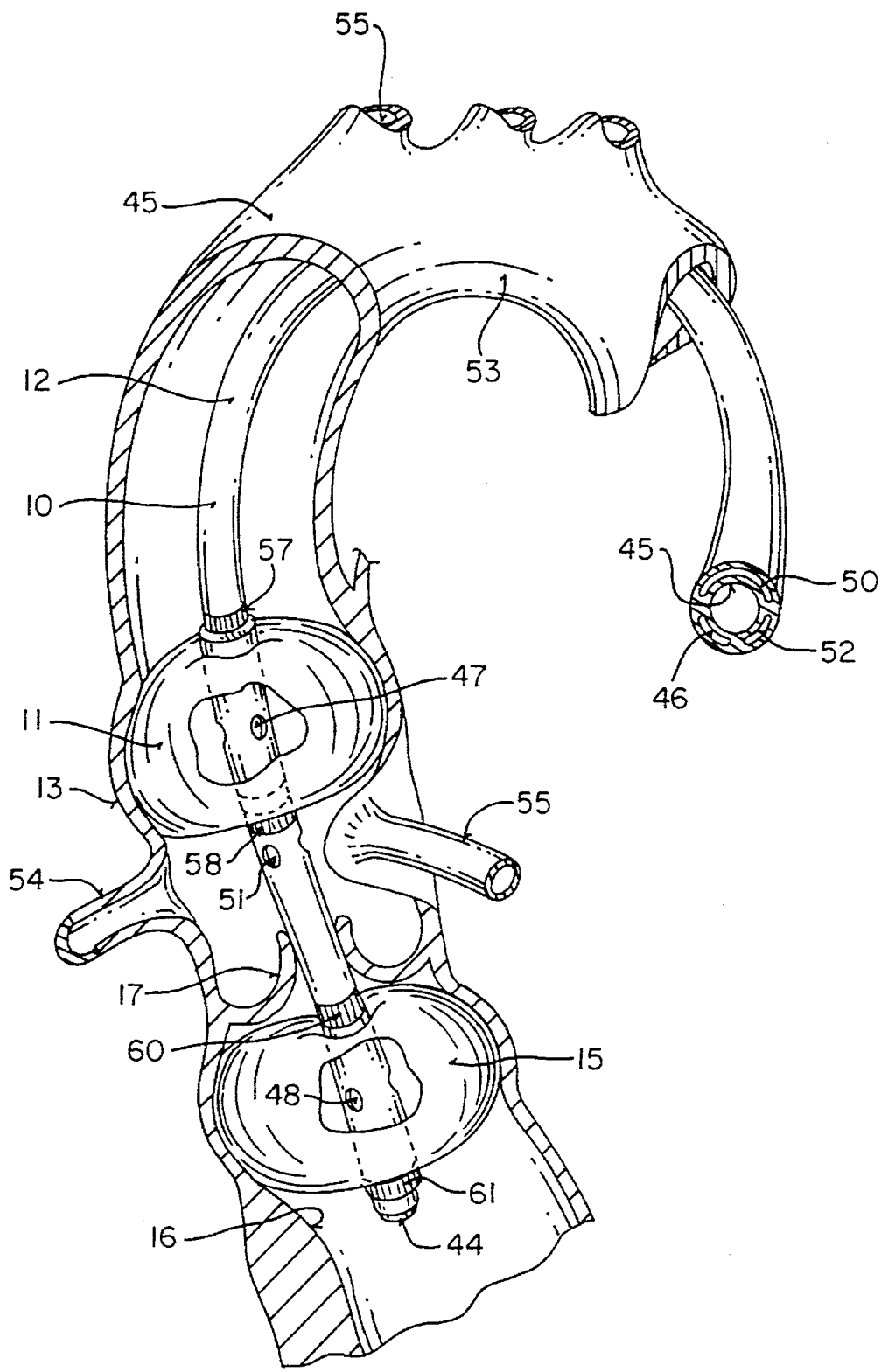
FIG. 7 is an enlarged view, partially in section, of the occlusion catheter shown in FIG. 1 disposed within the ascending aorta and the left ventricle of a patient.

Reference is made to FIG. 1 which schematically illustrates the overall cardiac accessing system including the occlusion catheter 10 of the invention. The occlusion catheter 10 has an expandable occluding member 11 on a distal portion of the catheter shaft 12 which, when inflated as best shown in FIG. 7, occludes the ascending aorta 13 to separate the patient's heart from the rest of the patient's arterial system downstream therefrom. An expandable seating member 15 is disposed on the catheter shaft 12 distal to the occluding member 11 and when inflated within the left ventricle 14, seats within the aortic vestibule 16, usually on the upstream surface of the aortic valve 17, not shown in FIG. 1, and securely positions the distal portion of the catheter shaft 12 within the ascending aorta 13. A cardiopulmonary by-pass system 18 removes venous blood from the femoral vein 20 through blood withdrawal catheter 21 as shown, removes CO2 and oxygenates the blood and then returns the oxygenated blood to the patient's right femoral artery 22 through return catheter 23 at sufficient pressure so as to flow throughout the patient's arterial system except for the portion isolated by the expanded occluding member 11 on the occlusion catheter 10. Alternatively, return catheter 23 and occlusion catheter 10 both may be positioned in the same femoral artery (either right or left) by, for example, introducing occlusion catheter 10 through the interior lumen of return catheter 23, as described in co-pending application Ser. No. 08/162,742, filed Dec. 3, 1993, the complete disclosure of which is incorporated herein by reference. Suitable cardiopulmonary bypass systems, such as those described in U.S. Pat. Nos. 4,447,590 and 4,540,399, which are incorporated heroin by reference, are commercially available from, for example, Thermedics (Wobum, Mass.).

A retroperfusion balloon catheter 24 is disposed within the patient's venous system with the distal end of catheter 24 extending into the coronary sinus 25 to deliver a fluid containing cardioplegic material in a retrograde manner to the myocardium in order to paralyse the entire myocardium. Antegrade delivery of cardioplegic fluids may be performed through the occlusion catheter 10, as will be described in more detail below, in addition to or instead of retrograde delivery through the coronary sinus.

The proximal extremity 26 of the occlusion catheter 10 extends out of the left femoral artery 27 through a cut down 28 and is provided with a multi-arm adapter 30. The adapter 30 has one arm 31 to receive an inflation device 32, a second arm 33 with a main access port 34 through which instruments, angioscope, irrigation fluid and the like may be passed, and a third arm 35 to withdraw blood, irrigation fluid and the like and direct the withdrawn fluid to the blood filter/recovery system 36 through lines 37 and 38. A suitable valve or stopcock 40 is provided to open and close the bypass line 37 and direct the fluid passing through the bypass line to a discharge line 41. A return line 42 may be provided to return any filtered blood, which will be described hereinafter, to the cardiopulmonary bypass system 18.

The details of the occlusion catheter 10 are best illustrated in FIGS. 2–7. As shown therein, occlusion catheter 10 includes an elongated catheter shaft 12 which has a main inner lumen 43 extending in fluid communication with the distal port 44 on the distal end of the shaft and with the main access port 34 in the second arm 33 of the adapter 30 on the proximal end of the shaft (FIG. 1). The main lumen 43 and the distal port 44 may be used to pass surgical instruments, angioscopes, irrigation and aspiration lines and the like into the ventricle region distal to the distal end of the catheter shaft 12. A supporting coil (not shown) may provided in the distal portion of the main or first inner lumen 43 or embedded in the wall of shaft 12 around inner lumen 43 to prevent the distal portion of the catheter shaft 12 from kinking as it is advanced through the patient's aortic arch. The shaft 12 is also provided with a second inner lumen 46 which is in fluid communication with the interior of the occluding member 11 through port 47 and the interior of the expandable seating member 15 through port 48. A third inner lumen 50 may be provided within the shalt 12 to direct fluids, e.g. cardioplegic or irrigation fluids, to the region of the ascending aorta between the occlusion and seating members 11 and 15 through ports 51 between occluding member 11 and seating member 15. Inner lumen 50 and ports 51 may also be configured to allow interventional devices such as angioplasty or atherectomy catheters to be introduced through lumen 50 and port 51 into the aorta and/or coronary arteries.

Occlusion catheter 10 will preferably be dimensioned and configured for introduction into a femoral artery and advancement to the ascending aorta and left ventricle of the heart through the iliac artery, descending aorta and aortic arch. This will generally require a length of at least about 80 cm, and usually about 90–100 cm. Alternatively, the occlusion catheter 10 may be adapted for introduction into the brachial or carotid arteries and advancement through the brachiocephalic artery into the ascending aorta, wherein the catheter may be substantially shorter in length, e.g., 20–60 cm.

Occluding member 11 is separated from seating member 15 by a distance selected to allow the occluding member to be positioned in the ascending aorta between the coronary ostia and the brachiocephalic artery when the seating member is expanded and seated adjacent the upstream side of the aortic valve within the left ventricle of the heart. Usually, the distal end of occluding member 11 will be separated from the proximal end of seating member 15 by a distance in the range of 1 cm to 8 cm, and preferably between 3 cm and 5 cm.

In one presently preferred embodiment shown in FIGS. 5 and 6, the catheter shaft 12 has an additional inflation lumen 52 which allows for the independent inflation and deflation of the occluding member 11 and the seating member 15.

The occlusion catheter 10 shaft 12 may be formed of conventional materials such a polyethylene, polyvinyl chloride and the like. The occluding member 11 and seating member 15 likewise may be formed of conventional polymers such as polyethylene, polyethylene terephthalate, a polyolefinic ionomer such as Surlyn, which is available from E. I. DuPont, DeNemours & Co. or polyurethane.

FIG. 7 illustrates the catheter 10 disposed within the patient's aorta 53 with the distal portion of the catheter disposed within the ascending aorta 13. The occluding member 11, shown in the inflated condition, occludes the passageway through the ascending aorta 13 between the coronary arteries 54 and 55 and the brachiocephalic artery 56. The seating member 15 is inflated within the aortic vestibule 16 adjacent to the aortic valve 17. Radiopaque markers 57 and 58 facilitate the fluoroscopic observation of the ends of the occluding member 11 and the radiopaque marker 60 and 61 facilitate the fluoroscopic observation of the ends of the seating member 15.

To set up the cardiac access system as shown in FIG. 1, the patient is initially placed under a light general anesthesia. The withdrawal catheter 21 and the return catheter 23 of the cardio-pulmonary bypass system 18 are percutaneously introduced into the fight femoral vein 20 and the right femoral artery 22, respectively. The operation of the cardio-pulmonary bypass system 18 is initiated to withdraw blood from the femoral vein 20 through catheter 21, remove CO2 and oxygenate the blood and then pump the oxygenated blood through the return catheter 23 to the right femoral artery 22. With the bypass system 18 operational, a cut down 28 is made in the left groin to expose the left femoral artery 27. Occlusion catheter 10 is inserted into the left femoral artery through an incision therein and advanced upstream until the occluding member 11 on the distal end of the occlusion catheter 10 is properly positioned in the ascending aorta 13 between the coronary ostia and the brachicephalic arteries, and the seating member 15 is within the patient's left ventricle 14 upstream of the aortic valve. The seating member 15 may then be expanded within the left ventricle 14. Once seating member 15 is expanded, occlusion catheter 10 may be drawn in a downstream direction so as to seat seating member 15 within aortic vestibule 16, usually against the upstream surface of the aortic valve 17. The occluding member 11 may then be inflated to occlude the ascending aorta 13, causing blood which is pumped out of the left ventricle 14 (until the heart stops beating due to the cardioplegic fluid as discussed hereinafter) to flow through the distal port 44 into the main inner lumen 43 of the occlusion catheter 10. During the period in which the heart remains beating, seating member 15 remains securely seated within the aortic vestibule 16, preventing occlusion catheter 10 from being moved under the pressure of blood flowing out of the heart. The blood flows through the inner lumen 44 out the third arm 35 of the adapter 30 into the bypass line 37 and then into the blood filter and blood recovery system 36 through the valve 40 and line 38. For blood and irrigation fluids containing debris, thrombi and the like, the position of the valve 40 may be changed to direct the fluid through the discharge line 41.

Figure 8:
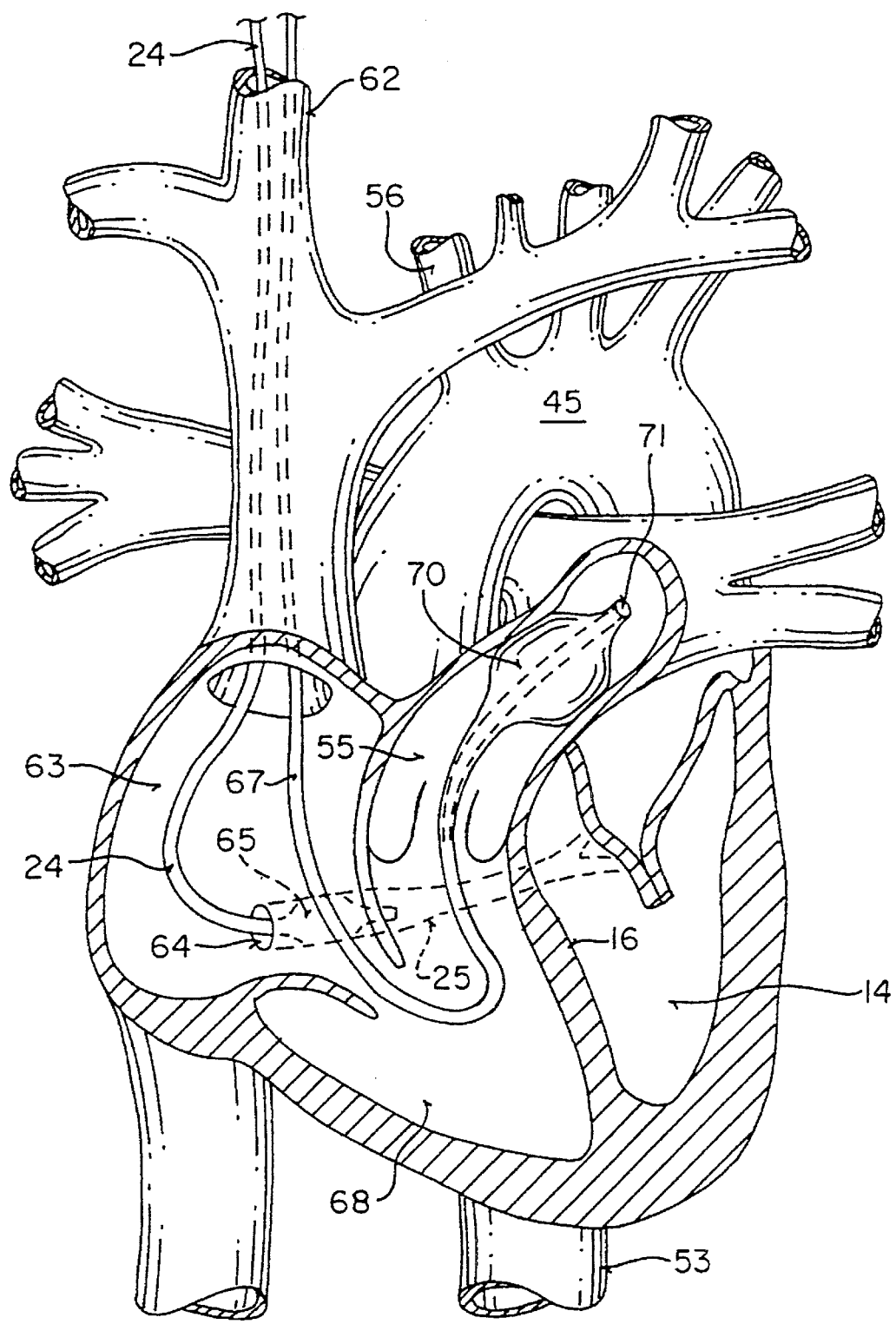
FIG. 8 is an enlarged elevational view, partially in section, of the heart shown in FIG. 1 illustrating in more detail the retroperfusing and pulmonary venting catheters.

As shown in FIG. 8, the retroperfusion catheter 24 is percutaneously inserted by a suitable means, such as the Seldinger technique, into the interior jugular vein 62 and advanced into the right atrium 63 and guided through the ostium 64 in the coronary sinus 25. The balloon 65 on the distal extremity of the retroperfusion catheter 24 is inflated to occlude the coronary sinus 25, to anchor the catheter 24 within the coronary sinus 25, and to prevent fluid loss through the ostium 64. A liquid containing a cardioplegic agent, such as KCl, is directed through the catheter 24 into the coronary sinus 25 and the pressure of the cardioplegic fluid within the coronary sinus 21 is maintained sufficiently high (e.g. 40 mm Hg) so that the cardioplegic fluid will pass though the coronary veins and the capillary beds to the coronary arteries. Cardioplegic fluid may also be infused through inner lumen 50 and distal ports 51 of occlusion catheter 10 to perfuse the myocardium through coronary arteries 54, 55 (FIG. 7). Once the cardioplegic fluid passes through the capillary beds into the myocardium, the heart very quickly stops beating. At that point, the myocardium is paralyzed and has very little demand for oxygen and can be maintained in this state for long periods of time with essentially no permanent damage by maintaining cardioplegic fluid within the myocardium. The flow of cardioplegic fluid through the capillary beds is maintained during the procedure and it is preferably maintained at a very low temperature, e.g. 40° C., to further reduce oxygen demand. Once the cardioplegic fluid flow through the myocardium is terminated and essentially all residue of the cardioplegic fluid has been flushed out with irrigation fluid such as saline, the heart will begin to beat on its own.

To minimize the flow of oxygenated blood into the left atrium and ultimately the left ventricle, the pulmonary trunk 66 is vented by advancing pulmonary venting catheter 67 through the internal jugular vein 62, the right atrium 63 and right ventricle 68 into the pulmonary trunk 66. The occlusion balloon 70 on the distal end of the pulmonary venting catheter 67 is inflated by inflation fluid to block the pulmonary trunk 66 and vent blood therein through distal port 71 and an inner lumen (not shown) extending the length of the catheter 67 to its proximal end where the blood is discharged through the proximal end of the catheter, which remains outside of the patient during the procedure. The venting of the pulmonary trunk 66 results in the decompression of the left ventricle 14. In the alternative, the venting catheter 67 may be provided with means on the exterior thereof, such as expanded coils as described in U.S. Pat. No. 4,889,137 (Kolobow), which hold open the pulmonary valve and perform the same function of decompressing the left ventricle 14. See also the article written by F. Rossi et al. in the *Journal of Thoracic Cardiovascular Surgery*, 1990; 100:914–921, entitled "Long-Term Cardiopulmonary Bypass By Peripheral Cannulation In A Model Of Total Heart Failure", which is incorporated herein in its entirety by reference.

Inflation of the occluding member 11 on the distal end of the occlusion catheter 10 fixes the distal portion of the catheter within the ascending aorta 13 and isolates the left ventricle 14 and pan of the ascending aorta including the ostia of coronary arteries 54, 55 from the rest of the arterial system downstream from the occluding member 11. Inflation of the seating member 15 firmly secures the distal portion of the occlusion catheter 10 within the ascending aorta 13. The passage of any debris or emboli generated during a cardiovascular procedure to regions downstream from the site would be precluded by the inflated occluding member 11 and/or seating member 15.

With the cardiopulmonary by-pass system in operation, the heart completely paralyzed and not pumping, the left ventricle decompressed and the ascending aorta blocked by the inflated occluding member 11 on the occlusion catheter 10, the heart is ready for a procedure to be performed. Procedures which may be performed using the occlusion catheter 10 of the invention include coronary artery bypass grafting, heart valve repair and replacement, septal defect repair, treatment of aneurism, pulmonary surgery, neurosurgical procedures, and various other procedures in which cardiac arrest and cardiopulmonary bypass are desirable.

In a preferred aspect of the invention, surgical instruments may be introduced through inner lumen 43 of occlusion catheter 10 into the left ventricle of the heart for performing cardiac procedures such as mitral valve repair and replacement, septal defect repair and the like, in the manner described in commonly-assigned copending application Ser. No. 07/991,188, which has been incorporated herein by reference. For example, an angioscope may be introduced through lumen 43 for visualization within the left ventricle or other heart chambers. Cutters, forceps, aspiration and irrigation tubes, suturing devices, heart valve prostheses and prosthesis introduction devices, as well as suturing, stapling or clip applying devices may be introduced through lumen 43 for purposes of, for example, replacing or repairing a malfunctioning mitral valve. Moreover, interventional devices may be introduced through lumen 50 and port 51 for performing procedures such as angioplasty, atherectomy, or aortic valve repair or replacement downstream of seating member 15. During such procedures, it may be desirable to deflate seating member 15 to facilitate access to the aortic valve 17 and/or aortic vestibule 16 to observe or perform a surgical procedure on these structures. After the procedure has been performed, seating member 15 may again be inflated to maintain the postion of occlusion catheter 10 as the heart is restarted. Advantageously, the invention provides an endovascular passageway to facilitate the performance of such procedures without the need for a gross thoracotomy as is required using conventional techniques.

Upon completion of the procedure, the cardioplegic fluid pumped through the retroperfusion catheter 24 or through lumen 43 of occlusion catheter 10 is changed to a compatible fluid, e.g. saline, containing no cardioplegic agents in order to flush out all of the cardioplegic materials from the myocardium. The pulmonary venting catheter 67 may be removed at the same time. Shortly thereafter, the heart begins to beat on its own and the blood coming into the right heart is pumped through the pulmonary trunk 66 to the lungs where it is oxygenated in a normal fashion. Oxygenated blood is returned from the lungs through the left atrium and into the left ventricle 14. Initially, the occluding member 11 and seating member 15 are maintained in the inflated condition, forcing the blood pumped out of the left ventricle to pass through the main inner lumen 43 of the occlusion catheter 10 taking with it debris, emboli and the like which may have formed during the procedure. The blood passing through inner lumen 43 may be directed through the third arm 35 of adapter 30, through the valve 40 and line 38 leading to blood recovery system 36 where the blood may be filtered and returned to the patient through the cardiopulmonary bypass system 18. Alternatively, the position of the valve 40 may be changed by means of arm 71 to discharge blood or other fluid containing tissue, embolism, debris and the like through discharge line 41. After sufficient time has elapsed to ensure that debris and embolism-free oxygenated blood is being pumped out of the left ventricle 14, the cardiopulmonary bypass system 18 is shut down and the occluding member 11 and seating balloon 15 are deflated to allow natural blood flow through the aorta.

The invention provides several advantages, including the ability to perform endovascular or thoracoscopic cardiac procedures while avoiding the need for a riskier, more expensive and complicated open-chest cardiac procedure. Further, even in those instances in which a thoracotomy is necessary, the present invention considerably reduces the risks involved. Additionally, the use of a seating member that is expandable within the left ventricle in conjunction with an aortic occluding member greatly enhances the postionability of the occluding member and its resistance to movement from pressure pulses while the heart is beating.

Unless described otherwise, the various components of the catheter and accessing system of the present invention can be formed of conventional materials using conventional procedures. The dimensions of the various components are selected so that they perform their intended functions in their intended environment. Moreover, while the invention has been described in terms of certain preferred embodiments, it will be apparent to those of ordinary skill in the art that many modifications and improvements can be made to the invention without departing from the scope thereof as defined on the appended claims.

What is claimed is:

1. An endovascular intra-aortic catheter system for providing access to a patient's heart through an aortic passageway leading away from an aortic valve in the patient's heart while isolating the heart from the patient's arterial system, comprising:

a) an elongated catheter shaft which is advanceable through the aortic passageway leading away from the aortic valve of the patient's heart, which has a proximal portion adapted to extend out of the patient and a distal portion adapted to be disposed within the patient's ascending aorta and left ventricle, and which has a first inner lumen extending therein from a port in the distal portion of the catheter shaft to a location in the proximal portion;

b) a first expandable member on the distal portion of the catheter shaft spaced proximally from the port in the distal portion which is dimensioned and configured so that it occludes the aortic passageway within the ascending aorta when expanded; and c) a second expandable member on the distal portion of the catheter shaft located proximally of the port in the distal portion and distally to the first expandable means and which is dimensioned and configured so that it seats within the left ventricle when expanded to secure the catheter as to minimize catheter movement within the aortic passageway, wherein said first and second expandable members are spaced-apart from each other by a distance sufficient to permit positioning in the aortic passageway and the left ventricle, respectively.

2. The catheter system of claim 1 wherein the first expandable member is an inflatable balloon having an interior which is in fluid communication with an inflation lumen extending within the catheter shalt from a location within the interior of the first expandable member to a location in the proximal portion which is adapted to extend out of the patient.

3. The catheter system of claim 1 wherein the second expandable member is an inflatable balloon having an interior in fluid communication with an inflation lumen extending within the catheter shaft from a location within the interior of the first expandable member to a location in the proximal portion which is adapted to extend out of the patient.

4. The catheter system of claim 1 wherein a second port is provided in the catheter shaft between the first and second expandable members and a fluid delivery lumen extends within the catheter shaft from the second port to a location within the proximal portion of the catheter shaft extending out of the patient.

5. The catheter system of claim 1 wherein the first and second expandable members are inflatable balloons having interiors, the catheter shaft further comprising an inflation lumen which is in fluid communication with the interiors of the first and second expandable members.

6. The catheter system of claim 5 wherein the inflation lumen extends to a location within the proximal shaft section which extends out of the patient.

7. An endovascular catheter system for providing access to a patient's heart through the patient's ascending aorta, comprising:
   a) an elongated catheter shaft which has at least one inner lumen extending therein and which is dimensioned and configured to be advanceable through an aortic passageway leading away from the patient's heart through the ascending aorta;
   b) a first expandable member on a distal portion of the catheter shaft which is dimensioned and configured to occlude the aortic passageway when expanded therein;
   c) a second expandable member on the distal portion of the catheter shaft, distal to the first expandable means, which is dimensioned and configured to seat within the left ventricle adjacent to the aortic valve when expanded to minimize movement of the catheter within the aortic passageway;
   d) a port in the distal portion of the catheter shaft distal to the second expandable member in fluid communication with the inner lumen which is adapted to withdraw fluid outside of the catheter into the inner lumen; and
   e) a second port in the catheter shaft between the first and second expandable members in communication with a second inner lumen extending within the catheter shaft and adapted to infuse a fluid into the aortic passageway between the first and second expandable members.

8. The catheter system of claim 7 wherein the first expandable member is an inflatable balloon having an interior in fluid communication with an inflation lumen extending within the catheter shaft.

9. The catheter system of claim 7 wherein the second expandable member is an inflatable balloon having an interior in fluid communication with an inflation lumen extending within the catheter shaft.

10. The catheter system of claim 7 wherein the first expandable member is an inflatable balloon having an interior in fluid communication with a first inflation lumen extending within the catheter shaft and the second expandable member is an inflatable balloon having an interior in fluid communication with a second inflation lumen extending within the catheter shaft, such that the first and second expandable members are independently expandable.

11. The catheter system of claim 7 wherein the first expandable member is separated from the second expandable member by a distance selected to allow the first expandable member to be positioned between the patient's coronary ostia and the patient's brachiocephalic artery when the second expandable member is seated adjacent an upstream side of the patient's aortic valve.

12. The catheter system of claim 1 wherein the distal side of the first expandable member is axially spaced-apart from a proximal side of the second expandable member by a distance in the range from 1 cm to 8 cm.

13. The catheter system of claim 12 wherein the distal side of the first expandable member is axially spaced-apart from a proximal side of the second expandable member by a distance in the range from 3 cm to 5 cm.

14. The catheter system of claim 7 wherein the distal side of the first expandable member is axially spaced-apart from a proximal side of the second expandable member by a distance in the range from 1 cm to 8 cm.

15. The catheter system of claim 14 wherein the distal side of the first expandable member is axially spaced-apart from a proximal side of the second expandable member by a distance in the range from 3 cm to 5 cm.

16. A system for preparing a patient for a cardiac procedure, comprising:
   a) an elongated aortic occlusion catheter adapted to be advanced to a location within a patient's ascending aorta, having proximal and distal ends, having a first inner lumen extending therein to a distal port in the distal end of the catheter, having a first expandable member on a distal portion thereof which when expanded within the patient's ascending aorta occludes the aortic passageway, having a second expandable member distal to the first expandable member which is configured so that it seats within the patient's left ventricle when expanded so as to minimize catheter movement within the aortic passageway, and having a second inner lumen extending therein to a perfusion port disposed between said first and second expandable members;
   b) a cardiopulmonary bypass system having means to withdraw blood from the patient's venous system, means to oxygenate the withdrawn blood and means to direct the oxygenated blood into the patient's arterial system; and
   c) means connected to the second inner lumen to deliver cardioplegic material to the patient's myocardium.

17. The system of claim 16 wherein the first expandable member on the elongated aorta occlusion catheter is an inflatable member.

18. The system of claim 17 wherein the elongated aortic occlusion catheter has a third inner lumen adapted to direct inflation fluid to the interior of the first expandable member.

19. The system of claim 16 wherein the second expandable member is an inflatable member.

20. The system of claim 19 wherein the elongated aortic occlusion catheter has a fourth inner lumen adapted to direct inflation fluid to the interior of the second expandable member.

21. The system of claim 16 wherein the elongated aortic occlusion catheter is adapted to withdraw blood from the left ventricle through the first inner lumen thereof and direct the withdrawn blood outside of the patient's body.

22. The system of claim 21 including means to return the withdrawn blood to the patient's vasculature.

23. A method of accessing a patient's coronary anatomy comprising:
   a) advancing to a location within a patient's ascending aorta and left ventricle an elongated catheter which has proximal and distal ends, which has an inner lumen extending therein to a port in the distal end and which has first and second expandable members on a distal portion thereof;
   b) expanding the first expandable member within the patient's ascending aorta between the coronary ostia and brachiocephalic artery to block blood flow therethrough; and
   c) expanding the second expandable member within the patient's left ventricle to seat the expanded second member therein.

24. The method of claim 23 further comprising paralyzing the patient's myocardium.

25. The method of claim 24 wherein the step of paralyzing comprises infusing cardioplegic fluid into the ascending aorta through at least one port in the catheter between the first and second expandable members so as to perfuse the patient's myocardium with the cardioplegic fluid through at least one coronary artery.

26. The method of claim 23 further comprising withdrawing fluid through the port in the distal end of the catheter and through the inner lumen to a location outside of the patient's body.

27. The method of claim 23 further comprising passing surgical instruments through the inner lumen of the catheter to a location within the patient's left ventricle.

28. A method for performing an endovascular cardiac procedure on a patient, comprising:

a) advancing to a location within a patient's ascending aorta and left ventricle an elongated delivery catheter which has proximal and distal ends, which has an inner lumen extending therein to a port in the distal end and which has first and second expandable members on a distal portion thereof;

b) expanding the first expandable member within the patient's ascending aorta between the coronary ostia and brachiocephalic artery to block blood flow therethrough; and c) expanding the second expandable member within the patient's left ventricle to seat the expanded second member therein;

d) withdrawing blood from the patient's venous system, oxygenating the withdrawn blood and returning the oxygenated blood to the patient's arterial system; and e) passing one or more instruments for performing the cardiac procedure through the inner lumen of the delivery catheter.

29. The method of claim 28 further comprising paralyzing the patient's myocardium.

30. The method of claim 29 wherein the step of paralyzing comprises infusing cardioplegic fluid into the ascending aorta through at least one port in the catheter between the first and second expandable members so as to perfuse the patient's myocardium through at least one coronary artery.

* * * * *